United States Patent [19]

Borrelli et al.

[11] 4,323,056

[45] Apr. 6, 1982

[54] RADIO FREQUENCY INDUCED HYPERTHERMIA FOR TUMOR THERAPY

[75] Inventors: Nicholas F. Borrelli, Elmira; Albert A. Luderer, Corning; Joseph N. Panzarino, Big Flats, all of N.Y.

[73] Assignee: Corning Glass Works, Corning, N.Y.

[21] Appl. No.: 151,210

[22] Filed: May 19, 1980

[51] Int. Cl.$^3$ .................. A61K 9/14; A61K 41/00
[52] U.S. Cl. .................. 128/1.3; 128/1 R; 128/260; 128/804
[58] Field of Search ............. 128/260, 1.3, 1.5, 804, 128/207.21, 419 R

[56] References Cited

U.S. PATENT DOCUMENTS

| | | | |
|---|---|---|---|
| 2,161,292 | 6/1939 | Hahnemann | 250/11 |
| 3,474,777 | 10/1969 | Figge et al. | 128/260 X |
| 4,106,488 | 8/1978 | Gordon | 128/1 R |
| 4,136,683 | 1/1979 | Gordon | 128/1.3 X |

FOREIGN PATENT DOCUMENTS

| | | | |
|---|---|---|---|
| 4406 | of 1874 | United Kingdom | 128/260 |
| 2024007A | 9/1980 | United Kingdom | 128/1.3 |
| 522688 | 5/1977 | U.S.S.R. | 128/1.3 |

OTHER PUBLICATIONS

Gilchrist, R. K., Potential Treatment of Cancer by Electromagnetic Heating, Surgery, Gynecoly & Obstetrics, Apr. 1960, pp. 499–500.

Thackray, P. C., et al., Indirect Heating Source for Treatment of Malignant Brain Tumors, Electro Component Science and Tech., vol. 1, No. 2, Dec. 1974, pp. 91–96.

MacLean, High Magnetic Fields in Cancer and Other Illnesses.

Primary Examiner—Robert W. Michell
Assistant Examiner—Nancy A. B. Swisher
Attorney, Agent, or Firm—Clinton S. Janes, Jr.

[57] ABSTRACT

The instant invention is directed to a noninvasive tumor treatment modality which results in a reduction of tumor mass and may lead to complete eradication of a tumor. The inventive method comprises localized magnetically-coupled, RF-induced hyperthermia mediated by a material which is non-toxic to and, preferably, compatible with animal tissue and has incorporated therewithin iron-containing crystals of such size, amount, composition, and magnetic properties to impart a coercive force of at least 200 oersteds to the material, and wherein the RF magnetic field has a frequency not in excess of about 10 kilohertz.

12 Claims, No Drawings

RADIO FREQUENCY INDUCED HYPERTHERMIA FOR TUMOR THERAPY

BACKGROUND OF THE INVENTION

It has been recognized that, when heat is applied to areas of animal tissue containing both normal and malignant cells sufficient to raise the temperature of such areas to the range of 41°-44° C., a preferential destruction of the malignant cells occurs. (Normal animal tissue is destroyed at a temperature of about 48° C.) Examinations of tumors subjected to such heat treatments utilizing light microscope and electron microscope techniques have revealed that the tumors undergo specific destruction with no substantial damage to adjacent normal cells such as fibroblasts and endothelial cells. The initial result of hyperthermia applied to solid in vivo tumors is the rapid increase of lysosomal enzyme activity in the cytoplasm of malignant cells with concomitant inhibition of respiratory metabolism. Significantly, a simultaneous depression of anaerobic glycolysis does not take place in the malignant cells, thereby promoting the accumulation of lactic acid first in the intracellular spaces and subsequently in the extracellular spaces. Inasmuch as most solid tumors exhibit slow exchange between intracellular fluid and blood, and this circumstance is particularly true in the central tumor regions, acidic conditions become predominant within the tumor during hyperthermia. This increase in acidity leads directly to enhanced lysosomal enzymatic activity (pH maxima 5-5.5). The nonmalignant cells surrounding the tumor sustain only minor and reversible damage. Both malignant and normal tissue demonstrate a rapid and marked inhibition of RNA synthesis which is subsequently followed by the partial inhibition of DNA and protein synthesis. A transitory effect on cell proliferation has also been observed. Nevertheless, those adverse effects are customarily eclipsed by the highly desirable rapid and pronounced lysosomal destruction occurring preferentially in the malignant cells. The biochemical lesion(s) affecting both RNA and DNA metabolism and the cells' ability to divide appear to be transient and are not believed to be the primary cause of hyperthermia-induced destruction. It has been postulated that a significant factor in normal cell survival resides in the anatomical location of those cells, i.e., the normal cells are located near the periphery of the tumor and are closely related to the blood vessels, thereby minimizing the buildup of acidity in their immediate environment. Hyperthermia has been found to interact synergistically with ionizing radiation treatment and chemotherapy, a factor which augments its clinical utility as an anticancer treatment modality.

The major obstacle impeding the widespread clinical utilization of hyperthermia in treating carcinomata has been the inability to deliver localized hyperthermia. Thus, early experimentation involving exposing an entire body to diathermy at temperatures of about 41° C. had evidenced a temporary regression of tumors, but shortly after the treatment the tumors began to grow rapidly again.

Attempts have been made to localize heating in the tumor-containing area with a minimum deleterious effect upon adjacent normal tissue through the use of such means as electromagnetic fields, e.g., lasers and microwaves, and radio frequency (RF) induced magnetic fields. The latter has been the subject of several publications, for example: "Selective Inductive Heating of Lymph Nodes", Gilchrist et al., *Annlas of Surgery*, 146, No. 4, pages 596-606, September, 1957; "Controlled Radio-Frequency Generator for Production of Localized Heat in Intact Animal", Medal et al., *American Medical Association Archives of Surgery*, 79, pages 83-87, September, 1959; and "Selective Heating and Cooling of Tissue in Cancer Chemotherapy", Shingleton et al., *Annals of Surgery*, 156, No. 3, pages 408-416.

Those publications described the implantation of powdered magnetic materials, specifically a magnetic form of iron oxide statedly defined as $Fe_2O_3$, into tissue. These particles became heated as a result of the coupling to the magnetic field through their dielectric and hysteresis loss. Those studies utilized magnetic fields at radio frequencies between about 0.12-2 megahertz.

Although initial experiments demonstrated that this method for localizing induction heating was operable in destroying metastases, two factors militated against this method being accepted as a useful modality for treating carcinomata. First, the magnetic form of iron oxide is insoluble in body fluids and in substantial concentrations may be toxic to and/or rejected by the body, and, second, the normal tissue surrounding the tumor became too hot during the heating operation and was subject to necrosis. This latter effect was due to dielectric heating, i.e., heating resulting from ionic conductivity of body tissue and fluids.

It has been recognized that more disparate heating between the suscepted region and the surrounding region would occur if the excitation field were of lower frequency. The heating of normal tissue takes place through dielectric heating which is a function of the field of frequency squared or even higher, depending upon the loss tangent, whereas magnetic hysteresis heating varies linearly with field frequency. Up to the present time, however, there has been no magnetic material with the necessary chemical, mechanical, and magnetic properties to be useful in contact with animal tissue while permitting the required heating to occur at reduced field frequencies.

OBJECTIVE OF THE INVENTION

The principal objective of this invention is to provide means for locally heating tumors in animal tissue to temperatures within the range of about 41°-50° C., depending upon the time of exposure, such that the malignant cells are preferentially destroyed with essentially no damage or toxic effect upon adjacent normal tissue.

SUMMARY OF THE INVENTION

We have discovered that this objective can be achieved through localized magnetically-coupled, RF-induced hyperthermia mediated by a material which is non-toxic to and, preferably, inert to or compatible with animal tissue and which has incorporated therewithin magnetic field suscepting crystals of certain size, composition, concentration, and magnetic properties. A magnetic field is utilized having a sufficiently low frequency that dielectric heating effects are reduced to a negligible level. The magnetic properties are such as to maximize the hysteresis loss, i.e., the material exhibits high magnetization, high coercive force, and high loop squareness, each of those characteristics contributing to hysteresis heating. Those magnetic properties are also consistent with the practical available field induced within simple induction coil configurations. The frequency of the magnetic field is maintained at a sufficiently low level that essentially only magnetic hysteresis heating can occur. Hence, the frequency of the magnetic field will generally be in the range of 10 kilohertz or below. The dielectric loss of animal tissue and fluids is small in this low frequency range thereby minimizing heating in the absence of a magnetic susceptor. The inventive materials disclosed herein promote effective magnetic hysteresis heating with no noticeable body rejection. This enhanced heating effect is due to the use of high concentrations of matrix material, this matrix material being essentially free from any toxic or inflammatory effect upon the animal body. Hence, the magnetic component is encapsulated in a matrix which is inert to or biocompatible with the animal body.

Iron-containing crystals have been determined to be the most desirable magnetic field susceptor material. Certain organic plastics, e.g., TEFLON ® FTP, have the necessary inertness and non-toxicity for useful matrix materials.

However, ceramic compositions selected from the group of glasses, glass-ceramics, and sintered ceramics which are non-toxic to and, preferably, compatible with animal tissue, and including in their structure magnetic crystals of iron-containing compounds, have been determined to constitute the most desirable target materials. It will be recognized that the effectiveness and efficiency of the materials are dependent upon their ability to translate magnetic energy into thermal energy, this ability being related to such factors as crystal type and concentration, the presence of precrystalline or semi-amorphous regions, and the like. Consequently, it will be apparent that bodies containing substantial quantities of ferrimagnetic crystals will be preferred. In general, the magnetic iron-containing crystals will consist of magnetite ($Fe_3O_4$) or a solid solution ferrite. However, any material, glass or crystalline, suitably encapsulated, having the required magnetic hysteresis response in low frequency RF fields will be operable. Moreover, inasmuch as the coercive force exhibited by the crystal phase varies with the size of the crystals, laboratory experience has indicated that the crystals should have a diameter in excess of 500 Å (to exceed superparamagnetic size) and, preferably, at least 10,000 Å (1 micron) to produce domain wall motion.

Customarily, the animal tissue will be heated to temperatures within the range of about 41°–44° C. inasmuch as those temperatures will cause necrosis of tumor tissue. In contrast, normal animal tissue is not destroyed until temperatures of about 48° C. are reached. It has been found, however, that brief exposures to temperatures up to about 50° C. can be tolerated with very little destruction of normal tissue. Such higher temperatures quickly destroy tumor cells so the time of the treatment can be significantly reduced. Hence, a series or pulses of RF magnetic energy can be utilized; the time of each pulse effective to induce necrosis of tumor tissue with virtually no effect upon normal tissue can be determined empirically. The concentration of ceramic necessary to induce the desired heating effect can also be determined empirically. Thus, the upper temperature of heating can be controllably limited by suitably selecting the ceramic and regulating the quantity thereof administered.

Glasses and glass-ceramics of diverse base constituents, e.g., silicates, aluminosilicates, borosilicates, borates, and phosphates, and containing iron oxide in significant amounts are known to the art. When batch materials for such glasses are melted under oxidizing or neutral conditions, the resulting glasses can exhibit magnetic behavior, the magnitude of the behavior being a function of glass composition, annealing schedule, presence of a minor amount of magnetic crystallization, etc. When glass melts are appropriately quenched or glass bodies subsequently exposed to the proper heat treatment, minute crystals structurally similar to magnetite can be developed and/or caused to grow in size within the glassy matrix and the ferromagnetic behavior then evidenced by the bodies is substantially enhanced. Glass-ceramic bodies are generally highly crystalline, i.e., greater than 50% by volume crystalline. The following patents are illustrative of such products.

U.S. Pat. No. 3,193,503 discloses the production of glass-ceramic articles consisting essentially, expressed in weight percent on the oxide basis, of 16–50% MgO, 37–60% $Fe_2O_3$, 20–45% $SiO_2$, and 0–15% of mineralizers or nucleants such as $CaF_2$, CoO, NiO, $V_2O_5$, $MoO_3$, and $ThO_2$. The resultant articles were termed "magnetic ceramic ferrites" but no crystallization identification data were supplied.

U.S. Pat. No. 3,694,360 describes the manufacture of glass-ceramics demonstrating ferrimagnetic properties. The compositions operable therefor consisted essentially, expressed in parts by weight on the oxide basis, of 35–55 $Fe_2O_3$, 5–15 $Li_2O$, 10–50 $SiO_2$, and 1–15 ZnO. The predominant crystal phase was stated to comprise a lithium ferrite.

U.S. Pat. No. 3,492,237 discussed glass-ceramic bodies having compositions within the $Li_2O$-$Na_2O$-$Al_2O_3$-$Fe_2O_3$-$SiO_2$ system wherein lithium ferrite is a primary crystal phase. The operable formulations have a mole ratio of $SiO_2$:$Na_2O$:$Al_2O_3$ of 11–13:3–4:4–1 with 1–10 moles each of $Fe_2O_3$ and $Li_2O$ per mole of $Al_2O_3$.

U.S. Pat. No. 4,140,645 reports glasses and glass-ceramics containing crystals of $Fe_3O_4$ with, optionally, a transition metal ferrite, for example, cobalt ferrite and nickel ferrite. The operable glass compositions were categorized into two groups, expressed in terms of weight percent on the oxide basis:

(a) 2–10% $Na_2O$ and /or $K_2O$, 5–20% $B_2O_3$, 15–40% FeO, 0–32% $Al_2O_3$, and 35–65% $SiO_2$; and (b) 1.5–6% $Li_2O$, 10–40% FeO, 10–20% $Al_2O_3$, 45–66% $SiO_2$, 0–5% $TiO_2$ and/or $ZrO_2$, and 0–5% $B_2O_3$, at least 1% $B_2O_3$ being required when the proportion of FeO is less than 15%. Likewise, the operable glass-ceramic compositions were formulated from two groups, expressed in terms of weight percent on the oxide basis:

(a) 2–10% $Na_2O$ and/or $K_2O$, 5–20% $B_2O_3$, 15–40% FeO, 15–32% $Al_2O_3$, and 35–50% $SiO_2$; and (b) 1.5–6% $Li_2O$, 10–40% FeO, 10–20% $Al_2O_3$, 45–66% $SiO_2$, 0–5% $TiO_2$ and/or $ZrO_2$, and 0–5% $B_2O_3$, at least 1% $B_2O_3$ being required when the proportion of FeO is less than 15%.

Both the base glass and glass-ceramic compositions spontaneously precipitate $Fe_3O_4$ when the molten batches are cooled to a glass body. Subsequent heat treatment of the glass bodies gives rise to the in situ growth of silicate crystals, e.g., mullite, beta-quartz solid solution, and beta-spodumene solid solution, yielding a highly-crystalline glass-ceramic body. The $Fe_3O_4$ crystals can experience some grain growth during that heat treatment.

It will be appreciated that, as a matter of convenience, the above patents report the total iron oxide content of the cited materials, customarily present as a combination of FeO and Fe$_2$O$_3$, as either "FeO" or "Fe$_2$O$_3$". Hence, in the interest of simplicity and because analysis of the individual proportions of FeO and Fe$_2$O$_3$ tedious and knowledge of the precise content of each is unnecessary to the operation of the respective inventions, the full amount of the iron oxide present was expressed as either "FeO" or "Fe$_2$O$_3$".

Each of the above patents was directed to base glasses in the silicate system. Such compositions are operable in the present invention. However, whereas there have been publications of silicate-based glasses suitable for bonding to bone or other living tissue, e.g., U.S. Pat. No. 4,159,358 describing glasses consisting essentially, expressed in terms of weight percent on the oxide basis, of 40–60% SiO$_2$, 10–32% Na$_2$O, 10–32% CaO, 0–18% CaF$_2$, 0–20% B$_2$O$_3$, and 0–12% P$_2$O$_5$, it has long been recognized that, in general, phosphate-based glasses are more compatible with living tissue than are silicate-based compositions. Consequently, the preferred base glasses, glass-ceramics, and/or sintered ceramics of the present invention have compositions founded in the phosphate composition system.

The desired localized hyperthermia can be achieved through numerous ways. For example, an aqueous dispersion of the target ceramic material in very finely-divided form can be injected directly into a tumor and/or into normal tissue immediately adjacent to the tumor. Subsequent exposure by the defined RF induced magnetic field causes the target material to be heated.

In another embodiment, an aqueous dispersion of the powdered ceramic material is injected via intravenous or arterial routes at a site near or distal to the tumor. Blood flow acts to transport the ceramic to the site of the tumor. Assistance in localizing the injected magnetic material utilizing this method can be found by guiding the passage with a magnet.

In the case of surgical exposure of a tumor, the target material can be injected into or applied to the outside of the tumor. Hyperthermia will be induced through magnetic field induction heating before and/or after the incision has been closed. Thus, the treatment can consist of a series of exposures. The ceramic will desirably be inert or else harmlessly degraded by body fluids, the degradation occurring slowly enough to permit the ceramic to be at the tumor site for a substantial period of time. Hence, a succession of individual treatments with RF fields to secure localized heating can be conducted with only one implacement of mediating material.

It is possible to derivatize the target ceramic particles with tumor specific ions or with antibodies and/or other similarly bioactive molecules directed against the tumor, thereby causing specific localization of the ceramic in and/or around the tumor. Thus, agents specific to a particular tumor can be attached directly to the ceramic or through the use of chelating or other coupling agents.

The physical properties of tumors can also be utilized in localizing the target ceramic in the areas thereof. For example, tumors generally exhibit pH values either in the range of about 3–4 or in excess of about 8.5. The pH of normal body fluids is about 7.4. Accordingly, it is possible to design magnetic target ceramics which precipitate at the pH value demonstrated by a particular tumor. Thereupon, the precipitated ceramic can be heated with the RF magnetic field.

Yet another method contemplates presensitizing the ceramic material to have affinity for a tumor species and thereafter delivering the ceramic to the tumor site by injection, cannulation, magnetic guidance, and the like. Such presensitization can involve the surface of the ceramic or the bulk thereof. For example, the ceramic can be etched and the pores filled with the sensitizing agent. Illustrations of such sensitizing agents include gallium for lung carcinomata and K/Mg for low pH tumors.

DESCRIPTION OF THE PREFERRED EMBODIMENTS

Table I records several glass compositions, analyzed in terms of weight percent on the oxide basis, operable in the instant invention. The actual batch ingredients therefor may comprise any materials, either oxides or other compounds, which, when melted together with the other components, will be converted into the desired oxide in the proper proportions.

The batch ingredients were compounded, ballmilled together to assist in achieving a homogeneous melt, and the mixture charged into silica, porcelain, MgO, or platinum crucibles. The crucibles were introduced into a furnace operating at 1300°–1550° C. and the batch ingredients melted together for about one hour. Thereafter, the melts were poured onto a water cooled steel mold and the melt quenched by a steel platen being immediately placed into contact with the top surface thereof. (In Examples 5–11 all the iron is reported in terms of Fe$_2$O$_3$.)

TABLE I

|  | 1 | 2 | 3 | 4 | 5 | 6 |
|---|---|---|---|---|---|---|
| Fe$_2$O$_3$ | 55.0 | 31.4 | 36.1 | 36.2 | 34.4 | 19.3 |
| FeO | 4.4 | 11.5 | 18.3 | 12.8 | — | — |
| P$_2$O$_5$ | 23.7 | 21.9 | 22.9 | 18.8 | 37.0 | 47.4 |
| Li$_2$O | 11.6 | 10.2 | — | 7.8 | 15.3 | 19.2 |
| SiO$_2$ | 3.4 | 13.3 | 6.2 | 11.9 | 10.1 | — |
| Al$_2$O$_3$ | 0.4 | 11.5 | 5.5 | 11.0 | 0.26 | 12.9 |
| MnO | — | — | 10.4 | — | — | — |
| B$_2$O$_3$ | — | — | — | 2.0 | — | — |
| MgO | — | — | — | — | 2.38 | 0.25 |

|  | 7 | 8 | 9 | 10 | 11 |
|---|---|---|---|---|---|
| Fe$_2$O$_3$ | 31.0 | 35.0 | 40.5 | 35.4 | 30.0 |
| P$_2$O$_5$ | 30.5 | 26.6 | 18.4 | 26.3 | 26.6 |
| Li$_2$O | 14.4 | 14.4 | 0.08 | 14.4 | 12.0 |
| SiO$_2$ | 18.8 | 20.0 | 10.8 | 14.2 | 16.6 |
| Al$_2$O$_3$ | 0.66 | 1.23 | 0.15 | 0.14 | 13.7 |
| MnO | — | — | 18.1 | — | — |
| B$_2$O$_3$ | — | — | — | 4.84 | — |
| MgO | 4.68 | 4.46 | 10.3 | 5.46 | 2.81 |

No Al$_2$O$_3$ was present in the batch materials for Examples 1, 5, and 7–10, no Li$_2$O was batched in Example 9, and no MgO was included in the batch of Example 6. The analyzed values recorded of those components constitute impurities which were most likely picked up from the crucibles during melting.

The melts crystallized upon cooling and X-ray diffraction analyses were conducted upon the resultant products of Examples 1–4. Example 1 appeared to be almost completely crystallized, the major phase being hematite (Fe$_2$O$_3$) with a minor amount of what is believed to be a lithium iron phosphate. The pattern of the latter phase did not identically match any published standard. Example 2 exhibited substantially more vitreous phase and the crystals appeared to consist of about 60% lithium ferrite (believed to have the stoichiometry of LiFe$_3$O$_8$) and 40% of what has been conjectured to be a lithium-doped magnetite. Thus, a slight shift in the Fe$_3$O$_4$ peak was observed. Example 3 also contained a significant amount of glassy phase with the bulk of the crystals demonstrating a diffraction pattern very close to that of magnetite. The presence of manganese in the starting materials suggests the possibility of manganese-doped magnetite or a small amount of manganese ferrite. Example 4 appeared to have a microstructure similar to that of Example 2, the crystal phase consisting primarily of lithium ferrite and the postulated lithium-doped magnetite. It has been hypothesized that $B_2O_3$ may be substituted in part for $Li_2O$ in the crystal phase. When placed in a magnetic field, Example 2 demonstrated the greatest activity followed by Example 4, Example 3, and Example 1, in that order.

Table II reports qualitative measurements of magnetism demonstrated by the exemplary compositions of Table I along with a determination of the magnetization exhibited by those compositions in a field of 700 oersteds ($M_{700}$). A measurement of the heating value (calories/loop/gram), as determined from the area under the hysteresis loop, is tabulated for Examples 5-11. Finally, a qualitative judgment of the squareness of the hysteresis loop is provided for Examples 5-11.

TABLE II

| Example | Magnetism | $M_{700}$ | Cal./Loop/Gram | Squareness |
|---|---|---|---|---|
| 1 | | 2.9 | | |
| 2 | | 20 | | |
| 3 | | 18 | | |
| 4 | | 21 | | |
| 5 | Very slight | 0.42 | $1.76 \times 10^{-6}$ | Poor |
| 6 | Slight | 0.67 | $1.48 \times 10^{-6}$ | Good |
| 7 | Slight | 2.2 | $3.2 \times 10^{-6}$ | Very good |
| 8 | Strong | 6.2 | $2.48 \times 10^{-5}$ | Fair |
| 9 | Very strong | 8.7 | $4.36 \times 10^{-5}$ | Fair |
| 10 | Strong | 7.3 | $1.03 \times 10^{-5}$ | Excellent |
| 11 | Very strong | 13.26 | $2.0 \times 10^{-4}$ | Fair-good |

In general the preferred compositions useful in the inventive method will consist essentially, by weight as analyzed on the oxide basis, of about 10-70% $Fe_2O_3$, 10-60% $P_2O_5$, $Fe_2O_3 + P_2O_5 > 50\%$ but $<90\%$, 0-25% $Li_2O$, 0-25% $SiO_2$, 0-20% $Al_2O_3$, 0-60% $B_2O_3$, and 0-25% MgO. Where a ferrite crystal phase is desired, up to 25% of such metal oxides as CoO, NiO, and MnO may be included.

In the following studies illustrating the effectiveness of the instant invention, particles of Example 1 comprised the magnetic ceramic material and murine adenocarcinoma of the breast BW10232 was utilized as the tumor. Example 1 was milled to particles having an average size of ~2 microns or less and exhaustively washed in isotonic Dulbeccos phosphate buffered saline (DPBS) pH 7.2 to remove possible toxic by-products of the production and milling processes. Murine adenocarcinoma arose spontaneously in the mammary gland of a C57BL/6J (B6) inbred mouse at the Jackson Laboratories, Bar Harbor, Maine in 1958. Gross examination of the tumor reveals a soft, white, encapsulated mass with frequent hemorrhagic zones. The tumor is palpable approximately 7-10 days post inoculation of tumor brei (minced, finely-divided tissue with variable proportions of single cell and clumped cellular masses).

Cryopreserved tumor having a volume of about 1 cm$^3$ was obtained from the National Cancer Institute Division of the Cancer Treatment Contract Production Facility, Mason Research Institute, Worcester, Massachusetts. The tumor was stored at $-209°$ C. in a cryopreservative medium and shipped to the applicants in dry ice ($-78°$ C.). The tumor was briefly held at $-89°$ C. in a mechanical freezer until passed.

On the day of passage, the cryopreserved tumor was quick-thawed by immersing the frozen ampule into a beaker of distilled water at 37° C. The tumor brei was asceptically transferred to sterile tissue culture petri dishes and minced with sterile surgical scalpel blades. All manipulations were performed within a laminar flow containment hood recommended by the National Cancer Institute for oncogenic agents of undefined hazard. The finely-minced tumor was brought to a final volume of 1.5 ml with medium 199 (Grand Island Biological Company, Grand Island, New York), 15% C57BL/J6 normal serum and brought through a series of decreasing diameter syringe needles (18°→20°→23°→27°) until the tumor could be injected through a 27° tuberculin syringe. The initial subcutaneous inoculum (5-10% suspension) was divided equally between six C57BL/6J age matched male mice (Jackson Laboratory, Bar Harbor, Maine). In approximately 10 days a 1 cm$^3$ mass was grossly apparent in two of the six recipients.

Variable-sized tumors were asceptically dissected free from normal fascia, debrided of necrotic tissue, and washed in DPBS. The tumor was thereafter minced with sterile surgical scalpel blades, the brei diluted to an approximate 10% suspension with DPBS, and passaged through decreasing diameter syringes as previously described. Analyses of the single cell population employing a 140 micron orifice and a Coulter ZBI-H-4 channelyzer (Coulter Electronics, Hialeah, Florida) calibrated with 10 micron spheres indicated a skewed population range from 20-380 $\mu m^3$ with the majority of the cells ($\sim 55\%$) being greater than 80 $\mu m^3$. Zero point 2 ml of the 10% tumor suspensions ($1 \times 10^7$ of 80 $\mu m^3$ or larger cells) were inoculated subcutaneously in the inguinal region. The animals were closely monitored for appearance of tumor foci via palpation. Any tumor cells not used for passage were resuspended in cryopreservative medium (medium 199, 15% C57BL/6J normal serum, 10% DMSO) and refrozen to $-80°$ C. Tumors so frozen were fully capable of in situ growth when passaged after thawing.

The following is a general discussion of the experimental protocol performed in these studies. C57BL/6J male age matched mice were inoculated subcutaneously with 0.2 cc of a 10% tumor preparation in the left and right inguinal region. In most instances, a single left and right tumor focus developed and the inventive treatment was initiated when the tumors approached 4-5 mm diameter (34-65 mm$^3$ volume). The left inguinal region immediately adjacent to the base of the tumor was subcutaneously injected with the ceramic suspension. Injection of the ceramic was conducted very slowly to avoid excessive pressure buildup within the tissue. One injection site only was utilized in most cases because multiple injections tended to displace previously-injected ceramic out through the initial injection site. Multiple injections may be used if initial injection volumes are small. The right tumor received no ceramic but was exposed to a RF magnetic field. This action permitted the tumor-bearing animal to serve as both experimental and control.

Prior to exposure to a RF magnetic field, surface temperatures of the inguinal tumor receiving ceramic and the axillary region were measured utilizing a calibrated microthermistor. The mice were then placed inside a plexiglass restrainer and positioned within a ten-turn, water-cooled solenoidal induction coil having a diameter of 3.5" and a height of 8". A 30 KW GCCO motor generator was utilized to drive the coil at 10 kilohertz. The unit was capable of supplying up to 1400 oersteds within the coil. The mice were treated for five minutes at 10 kilohertz and 700 oersteds and thereafter removed from the restrainer. The surface temperatures of the treated tumor and the axilla or untreated (right) tumor were measured. In most instances, the mice received only one ceramic injection and one exposure to the magnetic field. The animals were monitored daily with tumor diameters being ascertained by means of a vernier caliper. In a few experiments, only one inguinal tumor was carried and the mice were randomly divided into ceramic treatment alone, ceramic plus RF magnetic exposure, or no treatment.

Table III illustrates the localized heating effect caused by the RF magnetically coupled induction of the subcutaneously implanted particles of Example 1. Hence, the average tumor surface temperature before treatment was 36.3° C., whereas immediately after treatment the average temperature was measured as 40.3° C. In contrast, when the axillary temperatures before and after treatment were measured, no significant increase in temperature was observed. Accordingly, these data clearly attest to the capability of magnetic ceramic materials to induce localized hyperthermia. Although the recorded surface temperature measured did not attain the preferred clinical hyperthermia rang of 42.5°–43° C., the temperature of tissue closer to the ceramic particles was unquestionably higher than 40.5° C. because of the tumor regression observed and described below.

Five C57BL/6J mice evidencing a single left inguinal tumor averaging about 8.2 mm in diameter were injected with 0.28 grams of Example 1 particles at the base of the tumor following the above protocol. Four animals, viz., a, b, c, and d, received a total body exposure to a RF magnetic field of 700 oersteds at a frequency of 10 kilohertz for five minutes whereas the fifth mouse, e, served as a ceramic-only control. Animals a and b (containing particles of Example 1 and being exposed to a RF magnetic field) exhibited growth after 13 days in excess of that demonstrated by e, the control sample not treated. However, animals c and d (containing particles of Example 1 and being subjected to a RF magnetic field) demonstrated about a twofold reduction in tumor volume on days 7 and 8 relative to animal e. To ascertain whether the observed diminution of growth rate was a reproducible result of the ceramic+RF magnetic field therapy, the double tumor bearing experimental protocol described above was preformed.

Five C57BL/6J mice, viz. f, g, h, i, and j, bearing single left and right inguinal tumors having an average diameter of about 5 mm were subcutaneously injected with 0.3 grams of Example 1 particles at the base of the left tumor only. After this injection the entire bodies of f, g, h, and i were exposed for five minutes to a 700 oersted RF magnetic field at a frequency of 10 kilohertz. Thus, animal j, containing ceramic particles but not treated, served as the control. In animals f, g, and h, the left tumor mass grew at a diminished rate relative to the non-treated right tumor. Animal h represented particularly interesting data since no detectable tumor was present on the right side at the time of the RF exposure, but after several days a focus appeared which rapidly outgrew the treated left side. Animal i responded poorly to treatment although gross examination after seven days revealed a reduced left (treated) mass when compared to the right (untreated) mass. Examination of the tumors in control animal j manifested essentially equivalent growth on both the left and right sides.

Eight days after treatment the animals were sacrificed and careful gross dissection of the mice was undertaken. An appreciable accumulation of ceramic was noted in the treated tumor area with little or no observable spreading. This latter finding was of especial importance since it indicated that the RF exposure can be effectively reapplied on subsequent occasions after the initial injection of ceramic particles.

The final weights of the tumors dissected clear of normal tissue and ceramic were measured. The data reported in Table IV clearly illustrate a tumor mass reduction factor (left side vs. right side) ranging from 1.81 to 4.81. Control animal j demonstrated similar left and right tumor masses with a ratio of 0.91.

Examination of the normal tissue immediately adjacent to the ceramic particles manifested essentially no evidence of necrosis resulting from the ceramic-mediated, magnetic field treatment.

TABLE III

| Animal | Ceramic Dose | Surface Temperature Before Treatment (°C.) | | Surface Temperature After Treatment (°C.) | |
| --- | --- | --- | --- | --- | --- |
| | | Tumor | Axilla | Tumor | Axilla |
| a | 0.28g | 36 | 37 | 42.5 | 37 |
| b | 0.28g | — | — | 40.5 | — |
| f | 0.30g | 36 | 36.5 | 40 | 37 |
| g | 0.30g | 37 | 37 | 38.5 | 38.5 |
| h | 0.30g | 37 | 37 | 43 | 38 |
| i | 0.30g | 35.5 | 36.5 | 37.5 | 36.5 |

TABLE IV

| Animal | Left Tumor Mass (g) | Right Tumor Mass (g) | Ratio Right Tumor Mass:Left Tumor Mass |
| --- | --- | --- | --- |
| f | 1.65 | 3.35 | 2.03 |
| g | 2.20 | 4.0 | 1.82 |
| h | 0.80 | 3.85 | 4.81 |
| i | lost* | lost* | — |
| j | 3.5 | 3.2 | 0.91 |

*Animal died on seventh day. Gross observation on seventh day indicated an approximate two-fold difference between left and right tumor masses.

The above studies, illustrating the absence of migration of the ceramic particles from the site of the subcutaneous injection, coupled with the excellent tumor mass reductions observed after a single five-minute RF exposure, clearly suggested that total tumor eradication could be possible where exposure times are increased and/or multiple treatments are applied. Moreover, a more highly magnetic ceramic would require less time to heat the tumor tissue to the hyperthermia range. The effectiveness of the ceramic can also be improved by increasing the coercive force thereof via the addition of such doping ions as cobalt into the ferritic structure.

In a single experiment with a C57BL/6J mouse utilizing the above protocol, 0.3 grams of Example 1 were injected intratumor and subcutaneously at the margins of an inguinal tumor. The body of the animal was then subjected for one hour to a 700 oersted field having a frequency of 10 kilohertz. Subsequent examination indicated essentially total eradication of the tumor mass, thereby substantiating the above hypothesis that total tumor extirpation is feasible utilizing the inventive method. Further experimental work has demonstrated that administering pure unencapsulated magnetic susceptor materials, e.g., magnetite, at one-half the dosage level utilized with the inventive materials produced gross inflammation and obvious rejection.

We claim:

1. A method for reducing the mass of a tumor comprising localized magnetically-coupled, RF-induced hyperthermia mediated by a material which is non-toxic to animal tissue and which has incorporated therewithin magnetic iron-containing crystals of such size, composition, concentration, and magnetic properties to impart a coercive force of at least 200 oersteds to said material, and wherein the frequency of said RF magnetic field will not exceed about 10 kilohertz, allowing essentially only magnetic hysteresis heating to occur.

2. A method according to claim 1 wherein said mediating material is a ceramic selected from the group consisting of glass, glass-ceramic, and sintered ceramic.

3. A method according to claim 2 wherein said ceramic is a glass having a base composition selected from the group of phosphates, silicates, and borates.

4. A method according to claim 2 wherein said ceramic is injected as a dispersion of fine powder into the tumor and/or into normal tissue immediately adjacent to the tumor.

5. A method according to claim 2 wherein said ceramic is injected as a dispersion of fine powder into a vein or artery at a site near or distal to the site of the tumor.

6. A method according to claim 5 wherein the passage of said ceramic material through a vein or artery is guided through the use of a magnet.

7. A method according to claim 2 wherein said ceramic material is derivatized with tumor specific ions or with antibodies and/or other similarly bioactive molecules directed against the tumor.

8. A method according to claim 2 wherein said ceramic material is designed to precipitate at the pH value demonstrated by the tumor.

9. A method according to claim 2 wherein said ceramic material is presensitized to have an affinity for the tumor species.

10. A method according to claim 1 wherein said iron-containing crystals consist essentially of magnetite or a ferrite.

11. A method according to claim 10 wherein said ferrite is selected from the group of lithium, cobalt, nickel, manganese, and barium ferrite.

12. A method according to claim 1 wherein said RF treatment is undertaken via a series of exposures.

* * * * *